United States Patent [19]

Kressner

[11] Patent Number: 5,289,604

[45] Date of Patent: Mar. 1, 1994

[54] ELECTRIC TOOTHBRUSH WITH DEMOUNTABLE BRUSH SECTION

[75] Inventor: Gerhard Kressner, Altenstadt/Höchst, Fed. Rep. of Germany

[73] Assignee: Braun Aktiengesellschaft, Frankfurt, Fed. Rep. of Germany

[21] Appl. No.: 855,707

[22] PCT Filed: Sep. 5, 1990

[86] PCT No.: PCT/DE90/00673

§ 371 Date: May 5, 1992

§ 102(e) Date: May 5, 1992

[87] PCT Pub. No.: WO91/07117

PCT Pub. Date: May 30, 1991

[30] Foreign Application Priority Data

Nov. 14, 1989 [DE] Fed. Rep. of Germany ....... 3937853

[51] Int. Cl.⁵ .................. A61C 17/34; A46B 13/02
[52] U.S. Cl. ............................ 15/22.1; 15/28; 403/313; 403/314; 403/326; 403/377
[58] Field of Search .............. 15/22.1, 23, 24, 28, 15/29, 97.1; 403/313, 314, 326, 374, 377

[56] References Cited

U.S. PATENT DOCUMENTS

| 1,420,388 | 6/1922 | Schworm | 15/23 |
| 2,259,797 | 10/1941 | Cohen | 15/28 |
| 2,911,660 | 11/1959 | Klemas et al. | 15/28 |
| 3,034,376 | 5/1962 | Gonzalez | 15/23 |
| 3,195,537 | 7/1965 | Blasi | 15/28 |
| 3,220,039 | 11/1965 | Dayton et al. | 15/28 |
| 3,848,336 | 11/1974 | Copeland | 15/28 |
| 4,291,547 | 7/1983 | Jackson, Jr. | |
| 4,827,550 | 5/1989 | Graham et al. | 15/28 |
| 4,827,552 | 5/1989 | Bojar et al. | 15/28 |
| 4,989,287 | 2/1991 | Scherer | 15/28 |
| 5,054,149 | 10/1991 | Shi-Hoe | 15/28 |

FOREIGN PATENT DOCUMENTS

| 0254397 | 1/1988 | European Pat. Off. |
| 7512030 | 10/1976 | Fed. Rep. of Germany |
| 2901136 | 1/1979 | Fed. Rep. of Germany |
| 1053275 | 2/1954 | France |

Primary Examiner—Edward Roberts
Attorney, Agent, or Firm—Fish & Richardson

[57] ABSTRACT

An electric toothbrush has a brush section which is demountable from a handle section that has a protruding brush drive shaft. Radial and axial securing of the brush section to the handle section is accomplished by structure separated by function, including radial securing structure at the base of the brush section that engages cooperating structure at the end of the handle section from which the drive shaft protrudes, and axial securing structure housed within the brush section that engages the protruding drive shaft of the handle section.

19 Claims, 5 Drawing Sheets

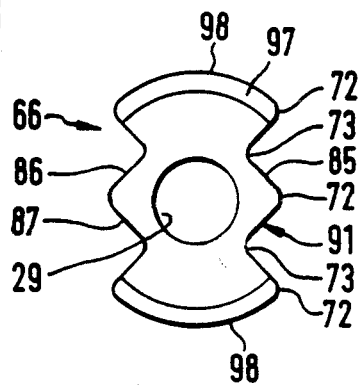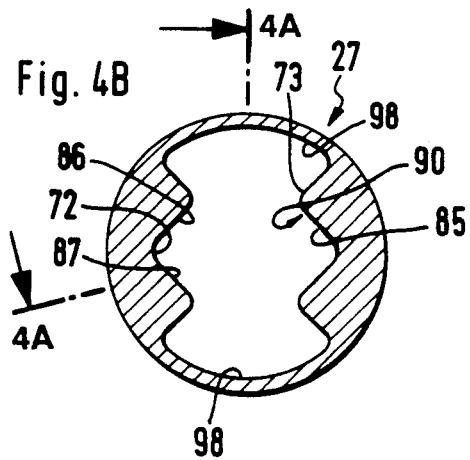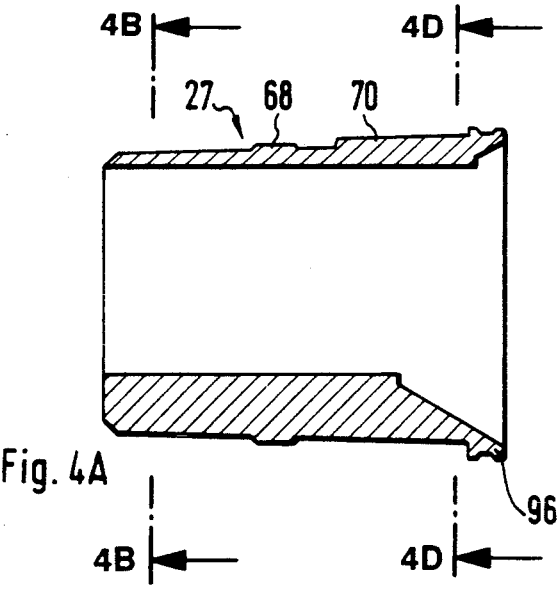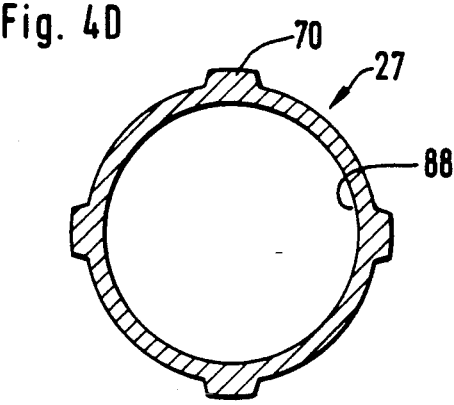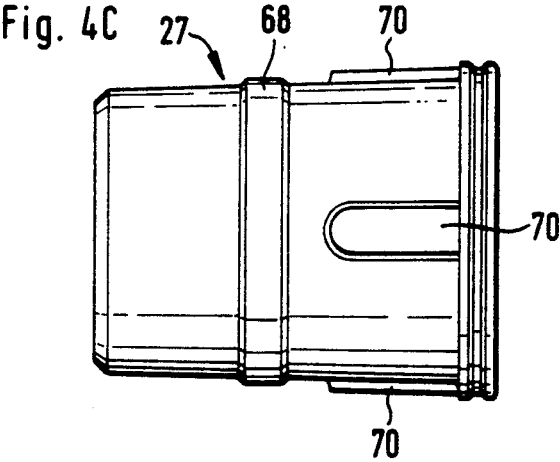

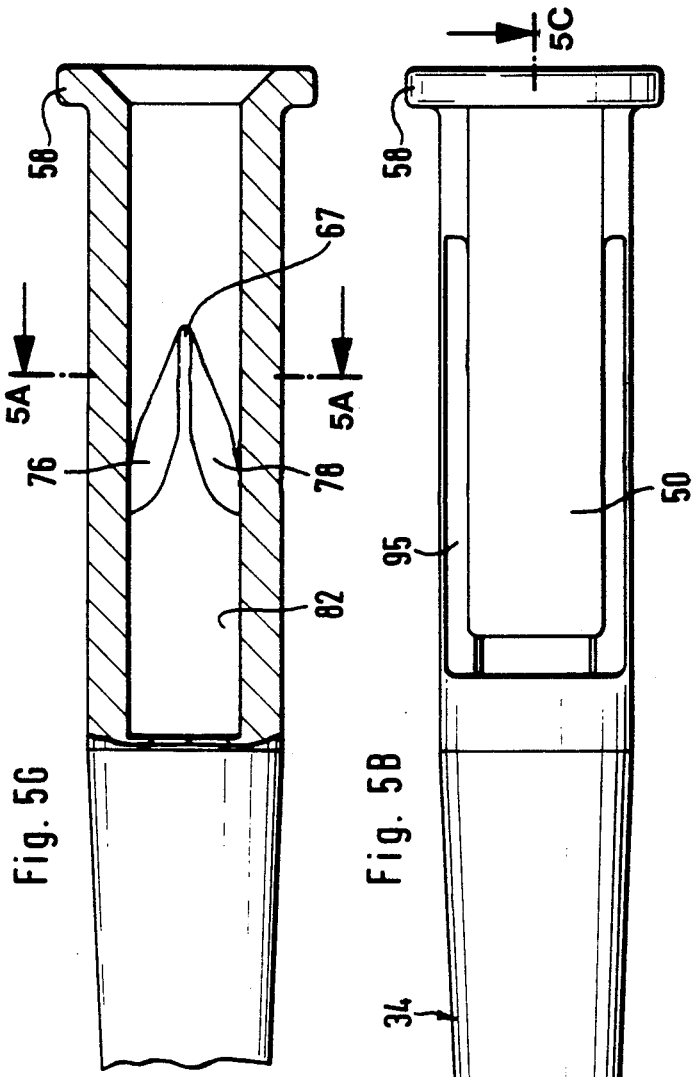
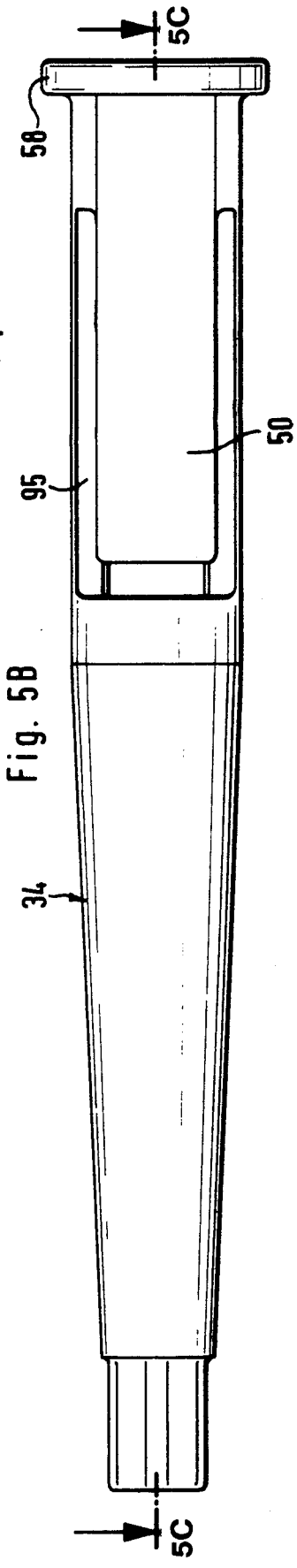
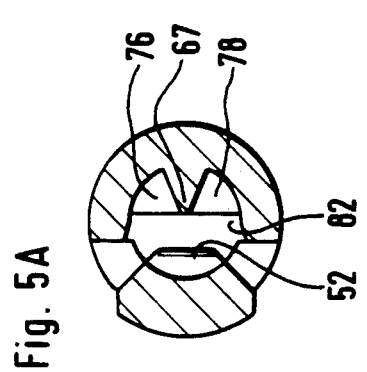
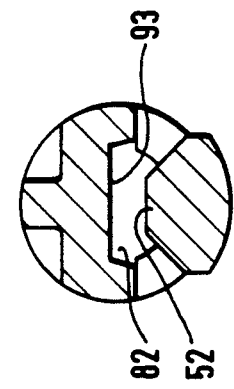

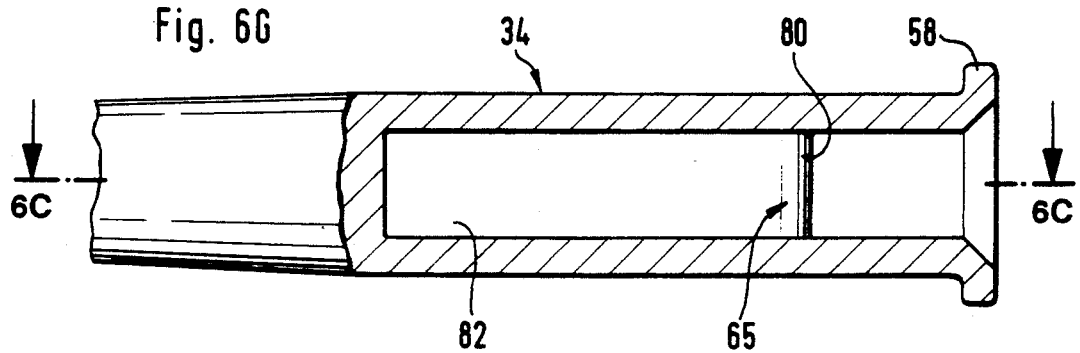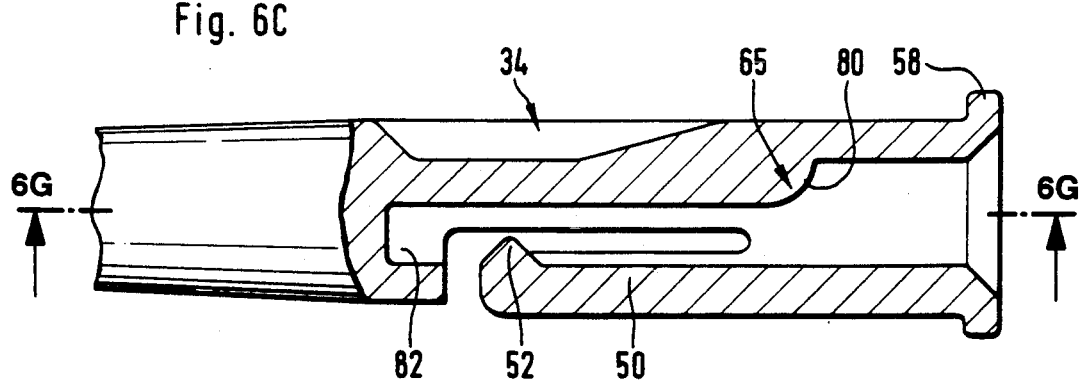

ELECTRIC TOOTHBRUSH WITH DEMOUNTABLE BRUSH SECTION

This invention relates to an electric toothbrush, comprising a handle section with an electric motor drive as well as a drive shaft and a brush section with a shaft for driving a rotary bristle supporting structure and a housing for receiving the shaft and mounting the bristle supporting structure. In this arrangement, the brush section is adapted to be connected to the handle section by coupling means for positioning the brush section in its proper location relative to the handle section, and the drive shaft is adapted to engage with the shaft by engaging means, with coupling means associated with the housing of the brush section and with the handle section being in relative cooperation.

An electric toothbrush incorporating these features is already known from U.S. Pat. No. 4,827,552. On the one hand, the demountable head section of this toothbrush must be secured axially in order to avoid inadvertent separation of the head section from the handle section during use of the toothbrush, for example. On the other hand, because the electric motor drive causes the bristle supporting structure or the brush to perform a rotary movement, it is also necessary to secure the housing of the head section against a radial movement relative to the handle section, in order to avoid that rotation of the shaft received by the housing rotates also the housing. In the known toothbrush, this radial and axial securing function is accomplished in that raised buttons provided on the handle section fit in corresponding dimples arranged on the housing of the head section. Locating the head section on the handle section in both axial and radial direction is thus accomplished by a single coupling means. This arrangement proves disadvantageous because tolerances in the positioning of the parts to be coupled, which are the brush section and the head section, as well as of the drive shaft and the driven shaft in the head section cannot be compensated for without difficulty. If the drive shaft and the driven shaft of the head section are not in accurate relative alignment, coupling the head section to the handle section is practically not possible without distortions occurring between the brush housing section and the handle section. Moreover, the housing sections of electric toothbrushes are generally injection-molded parts made of an industrial plastics material. In consequence, the use of relatively soft materials subjects the coupling means to a certain amount of wear, causing them to become inoperative in the course of use of the toothbrush.

It is an object of the present invention to improve upon an electric toothbrush incorporating the features initially referred to in such a manner that a reliable coupling of brush section and handle section is ensured while allowing certain tolerances in the relative positioning of the parts to be coupled It is a further object herein to arrange the coupling means such that a potential wear of the coupling means does not impair the operating capability of the toothbrush.

In an electric toothbrush of the type initially referred to, these requirements are satisfied in that the brush section is located relative to the handle section in an axial and a radial direction with respect to a longitudinal center line of the shaft by respective separate coupling means, with coupling means associated with the drive shaft and with the shaft being in relative co-operation.

As used in the present application, the terms coupling means and engaging means shall signify the following: Where the term "coupling means" is used, it shall mean a connection between the housing parts of the brush section and of the handle section. By contrast, the term "engaging means" denotes a connection between the drive shaft and the shaft in the brush section for the transmission of a torque.

Separating the coupling means by their function in a means serving only for radial location and another means serving only for axial location of the brush section relative to the handle section makes it possible to compensate for relative positional tolerances of the coupling parts. The parts to be coupled which include the means for axial location may have positional tolerances with regard to their relative radial location On the other hand, the parts including the coupling means for radial location of the brush section relative to the handle section may have axial positional tolerances relative to each other By these means, a safe and stress-free coupling of the brush section to the handle section can be accomplished while allowing certain tolerances in the relative positioning of the parts to be coupled, including, for example, the event that a drive shaft is not in alignment with the shaft in the brush section or that certain tolerances exist in the length of the shaft or drive shaft or the housing of the brush section. In addition, the separation of the coupling means by their function into means for axial and radial location makes it possible to arrange those coupling means which are subject to wear in parts of the toothbrush requiring replacement from time to time for reasons of hygiene or professional dental treatment. By configuring the coupling means of the drive shaft and the shaft as an axial securing means and the coupling means of the housing of the brush section and the handle section as a radial securing means for locating the brush section relative to the handle section, the radial securing means which is basically subject to little wear is placed in the area of the handle section of the toothbrush, while the axial securing means which is subject to greater wear is placed in the area of the shaft and the drive shaft, respectively. The drive shaft of electric toothbrushes is conventionally made of a non-wearing material as, for example, high-grade steel, while the shaft for driving a bristle supporting structure is made of a material which is more susceptible to wear as, for example, an industrial plastics material. The parts of the coupling means which are susceptible to wear are arranged in the area of the brush section which should be replaced after a certain period of time, at about two- to four-months' intervals, because of wear of the bristles of the bristle supporting structure mounted in the brush section or for reasons of hygiene.

Owing to the specific arrangement of the coupling means, the handle member of the toothbrush in which components of value such as accumulators, electric motor and gearing are received is not subject to wear resulting from the coupling of the brush section to the handle section. Because the axial securing function is performed by locking means on the shaft engaging in a complementary abutment means on the drive shaft, a robust structure of the axial securing means is obtained in which the locking means on the shaft which is susceptible to major wear is renewed anyway from time to time by replacing the brush section. The provision of means in a mounting sleeve of the shaft for receiving the drive shaft which force the shaft from any drive position into alignment with a predetermined coupling position during the coupling operation of the drive shaft to the shaft serves to couple the coupling members for axial location safely and readily. The fact that torques have to be transmitted between the drive shaft and the shaft in consequence of which load-transmitting surfaces have to be provided in the coupling area of the two shafts precludes the possibility for the two shafts to connect with each other in any relative position. The means for forced alignment of the shaft relative to the drive shaft which come into effect during the coupling operation of the two shafts facilitate the coupling of the two shafts in a particularly advantageous manner. These means for forced alignment may be implemented by right- and left-hand helicoidal surfaces arranged in a mounting sleeve of the shaft and co-operating with an end segment of the drive shaft having one side flattened, or alternatively, by a circular-segment profile which cooperates with a chamfer provided on the end segment of the drive shaft. Both means ensure a safe and forced alignment of the shaft relative to the drive shaft when the drive shaft is inserted in the mounting sleeve of the shaft, with the latter means affording particular ease of manufacture of the injection mold for the shaft Accomplishing a radial. Securing function by means of load-transmitting outer wall surfaces on the handle section which cooperate with corresponding complementary inner wall surfaces on the housing of the brush section has the advantage that any load introduced in the area of the radial securing means impinges on an area and that edge or point contact is avoided which might cause wear or damage to the housing in the area of the radial securing means. Especially when using industrial plastics material in the manufacture of the coupling parts for the radial securing means, the great advantage afforded by the relatively large areas of load impact to avoid damage or wear of the housing parts in the coupling area will be noticed By arranging adjacent load-transmitting surfaces at a relative angle of approximately 90°, an optimum introduction of load results in the coupling area of the radial securing means, irrespective of whether the drive shaft rotates clockwise or counterclockwise. Particularly if the shaft is driven so as to reverse direction, the arrangement of opposed load-transmitting surfaces at an angle of approximately 90° affords advantageous conditions in respect of the introduction of loads. Finally, joining the handle section and the housing section in the area of the radial securing means is accomplished simply and readily by configuring the transitions intermediate the individual adjacent load-transmitting surfaces as concave or convex part surfaces of a cylinder or cone.

Further advantages of the invention will become apparent from the subsequent description of embodiments in conjunction with the accompanying drawings.

In the drawings,

FIG. 3 is view of the housing shank taken along the line A—A of FIG. 2;

FIGS. 4a–d are various sections and a view of a shaped ring;

FIGS. 5 a,b,c,e,g are a view and various sections of the shaft 34 illustrating a first embodiment of the forced guiding means; and FIGS. 6 c,g are two sectional views illustrating a second embodiment of the forced guiding means.

Figure 1:
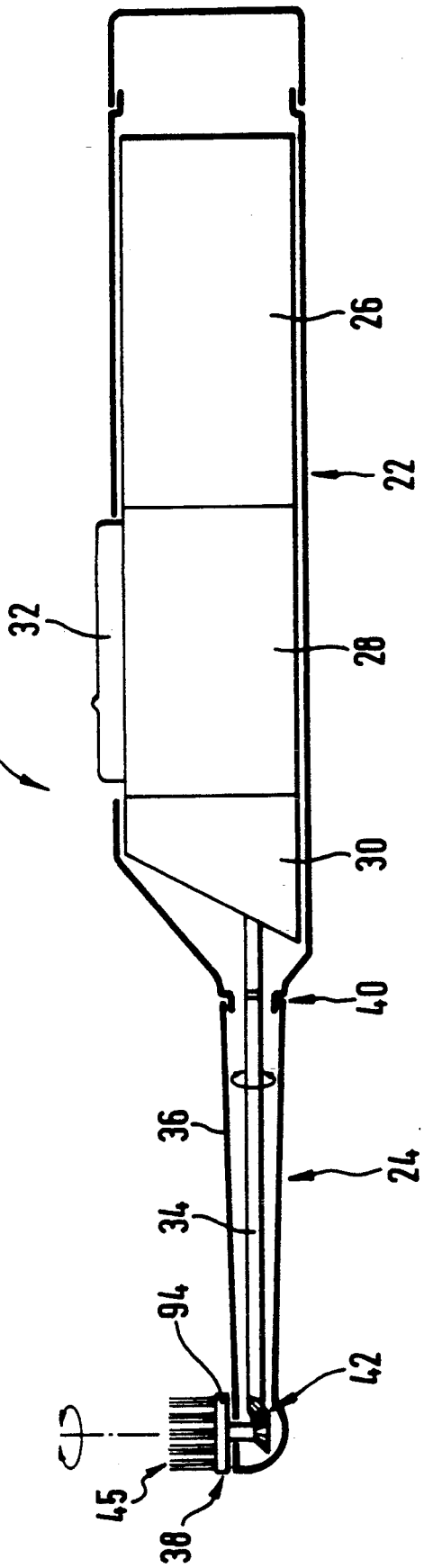
FIG. 1 is a schematic sectional view of an electric toothbrush with coupling means for connecting the brush section to the handle section.

Referring now to FIG. 1 of the drawings, reference numeral 20 identifies an electric toothbrush The toothbrush 20 comprises a handle section 22 and a brush section 24 which is adapted to be coupled together with the handle section 22 The handle section 22 houses an accumulator 26 or, alternatively, a battery, an electric motor 28 and a translating device 30 for converting the continuous rotary motion of the electric motor 28 into a rotary motion reversing direction in alternating sequence. On the outside of the handle section is a switch 32 for activating the toothbrush 20. The brush section 24 comprises a hollow mounting tube 36 receiving a shaft 34 The mounting tube 36 and the shaft 34 are adapted to be connected to the handle section 22 by coupling means 40 not shown in greater detail in FIG. 1 Arranged at the end of the brush section 24 remote from the handle section 22 is a bristle supporting structure 38 with a mounting plate 49 for receiving bristles 45 or tufts of bristles The bristle supporting structure 38 is driven by a bevel gear train 42 arranged at the head end of the shaft 34 The axis of rotation of the bristle supporting structure 38 defines an angle with respect to the axis of rotation of the shaft 34 of approximately 90°. It will be understood that this angle may also assume values of between 30° and 120° without limiting the scope of the invention. Via the bevel gear train 42, the torque of the direction-reversing rotary shaft 34 is transmitted to the bristle supporting structure 38 angled relative to the shaft 34. The range of the angle of rotation covered by the bristle supporting structure 38 may assume values on the order of between +/−20° and +/−100°, the preferred angle being, however, +/−35°, approximately.

Figure 2:
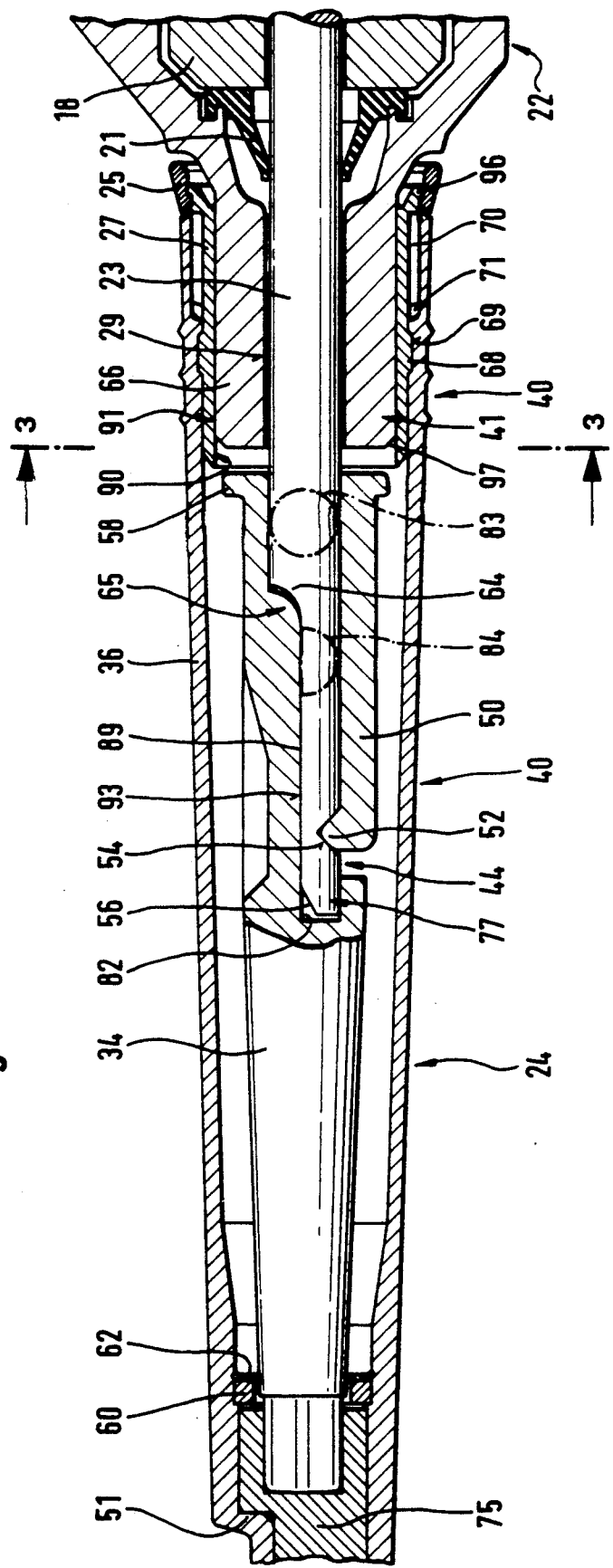
FIG. 2 is longitudinal sectional view of the toothbrush of FIG. 1 in the area of the coupling means.

FIG. 2 shows, in longitudinal section, the segment of the toothbrush 20 which is essential to the representation of the coupling means 40 The handle section 22 accommodates a housing inner portion 18 in which, among other parts, the drive means of the toothbrush are arranged A lip seal 21 disposed intermediate the housing inner portion 18 and the handle section 22 embraces the drive shaft 23 which is cylindrical in this area, preventing the entry of dirt and humidity in the interior of the handle section 22 The drive shaft 23 extends out of the handle section 22 through a central bore 29 of a housing shank 66 integrally formed with the handle section 22 In a transition area 64 of the drive shaft 23, the drive shaft 23 tapers in section from a circular cross section 83 to an approximately semicircular cross section 84 A planar surface 89 forming the boundary of the semicircular end segment 77 of the drive shaft 23 serves to transmit the torque of the drive shaft 23 to the shaft 34. The end segment 77 of the drive shaft 23 includes a chamfer 56 adjacent to the surface 89 A notch 54 is provided on the drive shaft 23 in the area of the end segment 77 opposite the surface 89

The brush section 24 comprises a slightly conically tapering mounting tube 36 receiving in its interior the shaft 34 At the end remote from the handle section 22, the shaft 34 is in positive engagement with a shaft member 75 serving to drive a bristle supporting structure not shown A shoulder 51 provided in the mounting tube 36 and a ring 60 held in the interior of the mounting tube 36 by means of a circlip 62 secure the shaft member 75 against axial displacement in the direction of a longitudinal center line of the shaft 34 or the drive shaft 23 The shaft 34 in turn is secured against axial displacements on the one side by the shaft member 75 and on the other side by a shaped ring 27 snapped into the mounting tube 36 at the end close to the handle section 22. The shaft 34 is located radially only in the area of its connection with the shaft member 75 with which it is at least in positive engagement In the area close to the shaped ring 27, the shaft 34 is not secured against radial excursions This enables the shaft 34 to change its angular position relative to the longitudinal center line of the drive shaft 23 to thereby compensate for certain tolerances as, for example, the deviation of position of a drive shaft 23 which is not in alignment with the ideal longitudinal center line In detail, axial securing of the shaft 34 is ensured in that an annular shoulder 58 formed integrally with the shaft 34 bears against an inner profile 90. (FIG. 4) of the shaped ring 27. To receive the drive shaft 23, the shaft 34 includes a mounting sleeve 82 whose inside cross section tapers from a circular cross section 83 to a semicircular cross section 84 complementary to the change of cross section of the shaft 23. In the transition area between these two shapes of cross section, means 65 are provided in the interior of the mounting sleeve 82 which force the shaft 34 from any drive position into alignment with a predetermined coupling position during the coupling operation between the drive shaft 23 and the shaft 34. Two preferred embodiments of these means are illustrated in greater detail in FIGS. 5 and 6. The inside cross section of the mounting sleeve 82 increases conically in the direction of the annular shoulder 58, thereby facilitating the insertion of the drive shaft 23 in the mounting sleeve 82. Extending over the outer circumference of the shaped ring 27 is an annular beading 68 cooperating with an annular groove 69 provided on the inner wall of the mounting tube 36 to serve as a fastening or locking means for locating the shaped ring 27 in its proper position in the mounting tube 36. The shaped ring 27 includes on its outer wall several axial longitudinal rib members 70 which engage in axial longitudinal grooves 71 provided on the inner wall of the mounting tube 36 By these means, the shaped ring 27 is locked against turning inside the mounting tube 36 Locking means 96 on the shaped ring 27 protrude from the shaped ring 27 to provide a fastening means for a colored ring 25, so that the individual users are in a position to identify their respective brush sections 24.

The inner profile 90 of the shaped ring 27 and an outer profile 91 of the housing shank 66 cooperate to function as a radial securing means 41 for connection of the mounting tube 36 to the handle section 22 such as to lock them against relative turning motions. The axial securing function of the brush section 24 relative to the handle section 22, that is, the securing of the brush section 24 against slipping off of the brush section 24 from the handle section 22 in the direction of the longitudinal center line of the drive shaft 23, is accomplished by providing a resilient tongue 50 on the shaft 34 in the area of the mounting sleeve 82, the tongue carrying a lug 52 at its resilient end. After the drive shaft 23 is introduced into the mounting sleeve 82, the lug 52 lockingly engages in the notch 54 of the drive shaft 23, thus providing for an axial location of the brush section 24 relative to the handle section 22.

The mode of operation of the radial securing means 41 will be explained in more detail in the following with reference to FIGS. 3 and 4 of the drawings. The view A—A of the housing shank 66 of FIG. 3 shows the special advantageous profiled structure of the side wall area of the housing shank 66. The basic shape of the housing shank 66 is a straight cylinder or a straight frustum of a cone, a frusto-conical shape involving tapering of the housing shank 66 in the direction of the head end of the handle section 22 to facilitate the insertion in the complementary shaped ring 27 The lead cam of the cylindrical or conical surface has a rotational symmetry of 180°, being formed by a circular arc 98 of 90° in two diametrically opposed areas. These circular arcs 98 of the lead cam are interconnected with each other via alternating concave and convex sections 73 and 72, respectively. Intermediate the concave sections 73 and the convex sections 72, the lead cam is formed by straight lines 85, 86, 87. In this arrangement, adjacent straight lines 86 and 87 as well as opposite mirror-image straight lines 86 and 85 define an angle with respect to each other of approximately 90°. This relative angle of the straight lines 85, 86 and 87 or the associated cylindrical or frusto-conical wall surfaces has shown to result in an optimum introduction of loads in the side wall surfaces of the housing shank 66, in particular if the drive shaft 23 is driven so as to rotate counterclockwise and clockwise, reversing direction in alternating sequence In the special embodiment of FIG. 3, the circular arcs 98 are interconnected at either end by two concave sections 73 and three convex sections 72 each. A chamfer 97 in the area of the cylindrical wall surfaces formed by the circular arcs 98 facilitates the insertion of the housing shank 66 in the shaped ring 27.

The inner profile 90 of the shaped ring 27 is configured to be complementary to the outer profile 91 of the housing shank 66, as becomes apparent particularly from the section B—B of FIG. 4. In the area of the locking means 96, the inside cross section 88 of the shaped ring 27 is circular (section D—D of FIG. 4), tapering conically and gradually changing into the inner profile 90 of the shaped ring 27. By this means, the insertion of the housing shank 66 in the shaped ring 27 is substantially facilitated.

On account of the particular configuration of the inner profile 90 of the shaped ring 27 and the corresponding complementary outer profile 91 of the housing shank 66, the torques or loads to be transmitted between the housing shank 66 and the shaped ring 27 are introduced into the respective components by area impact. Any line or point contact of the cooperating parts causing damage or increased wear of the surfaces of the parts is practically excluded. This advantage will come to bear in a particularly favorable manner especially with the materials used in the present embodiment—handle section 22 and shaped ring 27 being made of an industrial plastics material. The particular configuration of the embodiment with regard to the arrangement of the adjacent and/or opposite straight lines 85, 86 and 87 and the associated cylindrical or frusto-conical surfaces in an approximately rectangular relationship to each other is of advantage in particular if a direction-reversing rotary motion is to be transmitted from the drive shaft 23 to the shaft 34 However, the specific inner and outer profile 90 and, respectively, 91 also comes to bear advantageously if a continuous rotary motion, be it counterclockwise or clockwise, is to be transmitted from the drive shaft 23 to the shaft 34.

FIG. 5 shows the shaft 34 in detail. The outer wall of the shaft 34 is apertured in the form of a U-shaped cutout 95 in the area of the mounting sleeve 82, whereby a resilient tongue 50 is obtained The lug 52 integrally formed on the inner wall of the resilient tongue 50 engages in the notch 54 on the drive shaft 23 this locking engagement positioning the brush section 24 in its axial location relative to the handle section 22 The transmission of loads from the drive shaft 22 to the shaft 34 is ensured by means of the semicircular cross sections 84 of the drive shaft 23 and the receiving opening of the mounting sleeve 82, with the planar surfaces 89 of the drive shaft 23 being opposite to a surface 93 of the mounting sleeve 82. To facilitate the insertion of the drive shaft 23 in the mounting sleeve 82, the interior of the mounting sleeve 82 provides means for forcing the shaft 34 into alignment with the drive shaft 23, these means coming to bear as the drive shaft is inserted. In a first embodiment (FIG. 5), the forced guiding means comprise a wedge-shaped nose 67 provided in the inner wall area of the mounting sleeve 82 and lying diametrically opposite the resilient tongue 50. The nose 67 provides on either side helicoidal surfaces 76, 78, with the helicoidal surface 76 being left-handed and the helicoidal surface 78 being right-handed. The two helicoidal surfaces 76, 78 are generated by a straight line intersecting the longitudinal center line of the shaft 34 at right angles The helicoidal surfaces 76, 78 terminate in the planar surface 93. If, prior to coupling the brush section 24 to the handle section 22, the drive shaft 23 and the shaft 34 are out of relative alignment, such that the semicircular cross section 84 of the drive shaft 23 and the mounting sleeve 82 do not match, the surface 89 of the drive shaft 23 and the helicoidal surface 76 or 78 will cooperate such that the shaft 34 is automatically turned, into the appropriate coupling position, either to the right or to the left, when the drive shaft 23 is inserted in the mounting sleeve 82. By this means, it is possible to compensate for a relative rotary displacement of the drive shaft 23 and the shaft 34 of about $+/-90°$. A range greater than $+/-90°$ is not necessary in the present embodiment because the rotary motion of the shaft 34 and the drive shaft 23 is limited to a maximum range of $+/-70°$ about a zero position by means not shown. However, an extension of the "capture range" of the means 65 for forced guiding of the shaft 34 to cover a range of about $+/-180°$ is possible without further difficulty, for example, by providing the positive engagements of the drive shaft 23 with the mounting sleeve 83 with a rotational symmetry of 180° with respect to the longitudinal center line of the shaft 34. The "proper" coupling position of brush section 24 relative to handle section 22 is first determined in that the housing shank 66 has to be insertable in the shaped ring 27. Any relative rotary displacements of the drive shaft 23 and the shaft 34 in respect of this "proper" coupling position are then compensated for by the means 65 for forced alignment during the coupling operation A further embodiment of the forced guiding means 65 for the shaft 34 is shown in FIG. 6, with the remaining structure of the shaft 34 being unchanged Equally, the position of the sections G—G and C—C of FIG. 6 corresponds to the position of FIG. 5. The forced-guiding means 65 are configured as a circular-segment profile 80 which, in lieu of the wedge-shaped nose 67, is arranged opposite the resilient tongue 50 in the mounting sleeve 82. The chamfer 56 of the drive shaft 23 cooperates with this circular-segment profile 80. If the shaft 34 or the mounting sleeve 82 and the drive shaft 23 are not in fitting relative alignment, the inclined surface of the chamfer 56 exerts a torque on the shaft 34 through the circular-segment profile 80 when the drive shaft 23 is inserted in the mounting sleeve 82, in such fashion that the shaft 34 is automatically aligned to the proper coupling position. The configuration of the means 65 in accordance with the embodiment of FIG. 6 has the advantage over the embodiment of FIG. 5 that it allows a simpler structure of the injection mold for manufacture of the shaft 34. With regard to their effect, the means 65 of FIGS. 5 and 6 are substantially identical The invention finds application preferably, but not exclusively, in a toothbrush in which the bristle supporting structure 38 rotates vertically to the longitudinal center line of the brush section 24 at an angle of about $+/-35°$, reversing direction in alternating sequence, which is described in Ser. No. 07/855,640.

The separation by function of the coupling means for an axial as well as a radial location of the brush section 24 relative to the handle section 22 as described makes it possible to compensate for tolerances in the relative positioning of the parts to be coupled in an advantageous manner. Thus, for example, it is not necessary to locate the shaft 34 in the area of the annular shoulder 58 with respect to a radial excursion, thereby obviating the need for accurate alignment of the longitudinal center line of the drive shaft 23 with the longitudinal center line of the shaft 34. In addition, the possibility exists to place the locking means subject to wear—in particular, the lug 52 and the resilient tongue 50—in such parts of the toothbrush requiring frequent replacement anyway for medical or hygienic reasons, that is, the brush section 24. The handle section 22 being a long-lived, not replaceable part, has no locking means at all, so that it is not susceptible to wear caused by frequent coupling operations between the brush section 24 and the handle section 22.

I claim:

1. An electric toothbrush comprising
   (a) a handle section including an electric motor drive and a drive shaft;
   (b) a brush section including a brush shaft for driving a rotary bristle supporting structure and a housing for receiving said brush shaft as well as for mounting said bristle supporting structure;
   (c) engaging structure including a mounting sleeve for coupling said brush shaft with said drive shaft, said mounting sleeve including forcing structure for forcing said brush shaft from any drive position into alignment with a predetermined coupling position during the coupling operation of said drive shaft and said brush shaft;
   (d) coupling structure for connecting said brush section to said handle section, said coupling structure including means for positioning said brush section in its proper location relative to said handle section, with coupling structure associated with said housing of said brush section and with said handle section in relative cooperation; and
   (e) locking structure on said brush shaft engaging complementary abutment structure on said drive shaft for locating said brush section relative to said handle section in an axial and a radial direction with respect to a longitudinal center line of said brush shaft.

2. The electric toothbrush as claimed in claim 1 wherein said forcing structure is configured as right-hand and left-hand helicoidal surfaces which cooperate with an end segment of the drive shaft having one side flattened for forcing said brush shaft into alignment.

3. The electric toothbrush as claimed in claim 1 wherein said forcing structure is configured as a circular-segment profile cooperating with a chamfer provided on the end segment of said drive shaft for forcing said brush shaft into alignment.

4. The electric toothbrush as claimed in claim 1 wherein said coupling structure of said brush section housing and said handle section includes radial securing structure for locating said brush section relative to said handle section.

5. The electric toothbrush as claimed in claim 1 wherein said coupling structure includes load-transmitting wall surfaces of a profile on said handle section which cooperate with corresponding complementary wall surfaces of a profile on said brush section housing for providing a radial securing function.

6. The electric toothbrush as claimed in claim 5 wherein said profile includes adjacent planar wall surface sections arranged at a relative angle of about 90°.

7. The electric toothbrush as claimed in claim 6 wherein said profile includes two sets of opposed mirror-image planar wall surfaces, each said set including adjacent planar wall surface sections arranged at a relative angle of about 90°.

8. The electric toothbrush as claimed in claim 7 and further including a transition intermediate individual adjacent planar wall surfaces of said profiles, said transition being formed by convex sections or concave sections of a cylinder or frustrum of a cone.

9. An electric toothbrush comprising
(a) a handle section including an electric motor drive and a drive shaft;
(b) a brush section including a brush shaft for driving a rotary bristle supporting structure and a housing for receiving said brush shaft as well as for mounting said bristle supporting structure;
(c) engaging structure including a mounting sleeve for coupling said brush shaft with said drive shaft;
(d) coupling structure for connecting said brush section to said handle section, said coupling structure including means for positioning said brush section in its proper location and radial orientation relative to said handle section, with coupling structure associated with said housing of said brush section and with said handle section in relative cooperation; and
(e) locking structure on said engaging structure spaced from said coupling structure and engaging complementary abutment structure on said drive shaft for locating said brush section relative to said handle section in an axial direction with respect to the longitudinal center line of said brush shaft, said locking structure limiting separation of said brush section from said handle section in said axial direction.

10. The toothbrush of claim 9 wherein said handle section includes drive structure for rotating said drive shaft in rotary motion reversing direction in alternating sequence, said drive shaft includes a drive surface and said mounting sleeve includes cooperating surface structure for engaging said drive shaft surface for transmitting said alternating sequence rotary motion of said drive shaft to said brush shaft.

11. The toothbrush of claim 9 wherein said coupling structure includes structure for resisting rotation of said brush unit relative to said handle unit including profile structure with load-transmitting wall surfaces on said brush section which cooperates with corresponding complementary wall surfaces of profile structure on said handle section for providing said rotation resisting function.

12. The toothbrush of claim 11 wherein the load-transmitting wall surfaces of the profile structure of said brush section and the complementary wall surfaces of the profile structure of said handle section each includes adjacent planar wall surface sections, and wherein for each said profile structure the adjacent planar wall surface sections thereof are arranged at an angle of about 90° relative to each other.

13. The toothbrush of claim 11 wherein the load-transmitting wall surfaces of the profile structure of said brush section and the complementary wall surfaces of the profile structure of said handle section each includes two sets of opposed mirror-image planar wall surfaces, each said set including adjacent planar wall surface sections, wherein for each set of each said planar wall surfaces the adjacent planar wall surface sections thereof are arranged at an angle of about 90° relative to each other.

14. The toothbrush of claim 13 wherein each set of planar wall surfaces includes a transition wall section which connects adjacent planar wall surface sections thereof and which is formed by a geometrical section of a geometrical object, said geometrical section being selected from a group of sections including a convex section and a concave section, said geometrical object being selected from a group of geometrical objects including a cylinder and a frustrum of a cone.

15. The toothbrush of claim 11 wherein said handle section includes drive structure for rotating said drive shaft in rotary motion reversing direction in alternating sequence, said drive shaft includes a drive surface and said mounting sleeve includes cooperating surface structure for engaging said drive shaft surface for transmitting said alternating sequence rotary motion of said drive shaft to said brush shaft.

16. A demountable brush unit for coupling to a handle unit of an electric toothbrush, said handle unit having housing structure with an end surface, profile structure at said end surface, and a drive shaft protruding from said end surface, said drive shaft including a drive surface for transmitting rotary motion, said demountable brush unit comprising
elongated housing structure having first and second ends,
rotary bristle support structure disposed adjacent said first end of said housing structure,
coupling structure adjacent said second end of said housing structure for connecting said brush unit to said handle unit, said coupling structure including structure for resisting rotation of said brush unit relative to said handle unit including profile structure on said brush unit with load-transmitting wall surfaces of said profile structure which cooperate with corresponding complementary wall surfaces of profile structure on said end surface of said handle unit for providing said rotation resisting function,
brush shaft structure disposed within said housing structure for driving said rotary bristle support structure,
said brush shaft structure including mounting sleeve structure for receiving said protruding drive shaft of said handle unit, said mounting sleeve structure including an internal drive surface for engaging the drive surface of said drive shaft for transmitting rotary motion of said drive shaft to said brush shaft structure and further including a resilient structure for engaging said protruding drive shaft to releasably latch said mounting sleeve structure and said brush unit to said drive shaft of said handle unit and to thereby limit separation of said brush unit from said handle unit in an axial direction with respect to a longitudinal center line of said drive shaft.

17. The brush unit of claim 16 wherein the load-transmitting wall surfaces of said profile structure on said brush unit includes adjacent planar wall surface sections, said adjacent planar wall surface sections being arranged at an angle of about 90° relative to each other.

18. The brush unit of claim 16 wherein the load-transmitting wall surfaces of said profile structure on said brush unit includes two sets of opposed mirror-image planar wall surfaces, each said set including adjacent planar wall surface sections, wherein for each set of each said planar wall surfaces the adjacent planar wall surface sections thereof are arranged at an angle of about 90° relative to each other.

19. The brush unit of claim 18 wherein each set of planar wall surfaces includes a transition wall section which connects adjacent planar wall surface sections thereof and which is formed by a geometrical section of a geometrical object, said geometrical section being selected from a group of sections including a convex section and a concave section, said geometrical object being selected from a group of geometrical objects including a cylinder and a frustrum of a cone.

* * * * *